(12) United States Patent
Huchel et al.

(10) Patent No.: US 9,862,727 B2
(45) Date of Patent: Jan. 9, 2018

(54) PROCESS FOR CONTROLLING MALODORS USING OXAZOLIDINES

(71) Applicant: Henkel AG & Co. KGaA, Duesseldorf (DE)

(72) Inventors: Ursula Huchel, Cologne (DE); Marc Weyhe, Krefeld (DE); Lukas Baron, Essen (DE)

(73) Assignee: Henkel AG & Co. KGaA (DE)

(*) Notice: Subject to any disclaimer, the term of this patent is extended or adjusted under 35 U.S.C. 154(b) by 0 days.

(21) Appl. No.: 14/179,949

(22) Filed: Feb. 13, 2014

(65) Prior Publication Data

US 2014/0161757 A1    Jun. 12, 2014

Related U.S. Application Data

(63) Continuation of application No. PCT/EP2012/065638, filed on Aug. 10, 2012.

(30) Foreign Application Priority Data

Aug. 31, 2011  (DE) .................. 10 2011 081 871

(51) Int. Cl.
| | | |
|---|---|---|
| *C07D 498/08* | (2006.01) | |
| *A61L 9/01* | (2006.01) | |
| *C11D 3/50* | (2006.01) | |
| *A61L 9/14* | (2006.01) | |
| *C11D 3/00* | (2006.01) | |

(52) U.S. Cl.
CPC .............. *C07D 498/08* (2013.01); *A61L 9/01* (2013.01); *A61L 9/14* (2013.01); *C11D 3/0068* (2013.01); *C11D 3/507* (2013.01); *A61L 2202/26* (2013.01)

(58) Field of Classification Search
CPC ................................ A61L 9/01; C11D 3/0068
See application file for complete search history.

(56) References Cited

U.S. PATENT DOCUMENTS

| | | | |
|---|---|---|---|
| 4,277,353 A | | 7/1981 | Deen et al. |
| 5,929,022 A | * | 7/1999 | Velazquez ................ C11D 1/40 510/101 |
| 6,861,402 B1 | | 3/2005 | Miracle et al. |
| 2003/0158079 A1 | | 8/2003 | Dykstra et al. |
| 2003/0207786 A1 | | 11/2003 | Miracle et al. |
| 2004/0067870 A1 | | 4/2004 | Miracle |
| 2004/0087453 A1 | | 5/2004 | Dykstra et al. |
| 2008/0305063 A1 | * | 12/2008 | Huchel et al. .................. 424/65 |
| 2009/0312231 A1 | | 12/2009 | Huchel et al. |
| 2012/0309669 A1 | | 12/2012 | Huchel et al. |

FOREIGN PATENT DOCUMENTS

| | | |
|---|---|---|
| EP | 1787689 A1 | 5/2007 |
| WO | 2010/094356 A1 | 8/2010 |
| WO | 2010/142479 A1 | 12/2010 |

OTHER PUBLICATIONS

PCT International Search Report (PCT/EP2012/065638) dated Oct. 17, 2012.

* cited by examiner

*Primary Examiner* — Lanee Reuther

(74) *Attorney, Agent, or Firm* — Thomas G. Krivulka

(57) ABSTRACT

The invention describes a method for degrading off-odors by employing a special 1-aza-3,7-dioxabicyclo[3.3.0]octane compound. Degradation of off-odors to the point of extinction of the off-odor, on hard and/or soft surfaces, in particular on textiles, and in room air, is made possible.

12 Claims, No Drawings

PROCESS FOR CONTROLLING MALODORS USING OXAZOLIDINES

FIELD OF THE INVENTION

The present invention generally relates to a method for degrading off-odors preferably with regard to the treatment of hard and/or soft surfaces, and more particularly relates to the degradation of off-odors in the context of a textile treatment method, and likewise to the degradation of off-odors in room air.

BACKGROUND OF THE INVENTION

An important consumer requirement, which also plays a role e.g. in the utilization of washing, cleaning, or care-providing agents, consists in the elimination or at least diminution of bad odors (i.e. off-odors) or undesired odors. Off-odors derive from specific olfactorily active compounds that are also referred to as "malodorants." Malodorants are foul-smelling compounds having so-called kakosmophoric groups, e.g. amine derivatives and sulfur derivatives. The presence of such off-odors generally results in a negative effect on human comfort, and for that reason the consumer makes an effort to extinguish these odors. Often, however, the off-odors are not extinguished but merely masked. It is usual to use for this purpose products that contain volatile, usually pleasant-smelling substances, and that even in small quantities can mask foul odors.

U.S. Pat. No. 6,861,402 describes fragrance precursors that contain a fragrance aldehyde or a fragrance ketone in the form of an oxazolidine. For example, N-benzylethanolamine is reacted with a fragrance so that a monocyclic oxazolidine is produced. US 2003/0207786 A1 likewise describes fragrance precursors that have an oxazolidine structure. U.S. Pat. No. 4,277,353 describes mono- and bicyclic oxazolidines as corrosion-inhibiting additives for lubricating oils. US 2004/0087453 A1 describes specific photolabile fragrance precursors that can also be bound in the form of oxazolidines. US 2004/0067870 A1 describes special fragrance aldehydes having a tertiary alpha-carbon atom, which can also be bound in the form of oxazolidines. US 2003/0158079 A1 describes active-agent delivery systems suitable for delivering an active agent onto a substrate, the active-agent delivery system encompassing an active agent in the form of an aldehyde or ketone and an amine that encompasses a primary and/or secondary amine unit. WO 2007/087977 A1 describes 1-aza-3,7-dioxabicyclo[3.3.0]octane compounds whose use as fragrance precursors and employment in washing or cleaning agents is described. A method for degrading off-odors is not, however, mentioned therein.

WO 2010/094356 A1 describes specific copolymers, one of the monomers used being a 1-aza-3,7-dioxabicyclo[3.3.0]octane compound. These copolymers are used as fragrance precursors. A method for degrading off-odors is not, however, mentioned therein.

WO 2008/074598 A1 describes silicic acid esters to which scents constituting 1-aza-3,7-dioxabicyclo[3.3.0]octane compounds are bound. A method for degrading off-odors is not, however, mentioned therein.

The object of the present invention was to provide the consumer with a further capability for bringing about a degradation of off-odors.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A method for degrading off-odors by employing a 1-aza-3,7-dioxabicyclo[3.3.0]octane compound of the general formula (I)

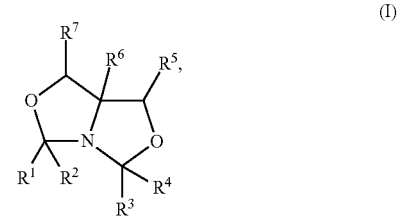

wherein
$R^1$, $R^2$, $R^3$, $R^4$ mutually independently denote residues that, in a compound of the general formula $R^1$—C(=O)—$R^2$ or $R^3$—C(=O)—$R^4$, yield a fragrance aldehyde having at least six, preferably at least seven, in particular at least eight carbon atoms or a fragrance ketone having at least six carbon atoms or a fragrance ketone having at least six carbon atoms,
$R^5$, $R^6$, $R^7$ mutually independently denote H or a hydrocarbon residue that can be acyclic or cyclic, substituted or unsubstituted, branched or unbranched as well as saturated or unsaturated.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The subject matter of the invention is a method for degrading off-odors by employing a 1-aza-3,7-dioxabicyclo[3.3.0]octane compound of the general formula (I)

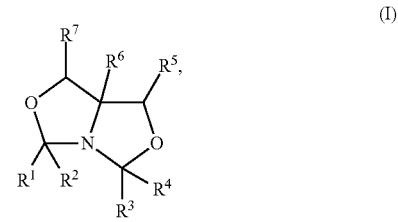

where
$R^1$, $R^2$, $R^3$, $R^4$ mutually independently denote residues that, in a compound of the general formula $R^1$—C(=O)—$R^2$ or $R^3$—C(=O)—$R^4$, yield a fragrance aldehyde having at least six, preferably at least seven, in particular at least eight carbon atoms or a fragrance ketone having at least six, preferably at least seven, in particular at least eight carbon atoms,
$R^5$, $R^6$, $R^7$ mutually independently denote H or a hydrocarbon residue that can be acyclic or cyclic, substituted or unsubstituted, branched or unbranched, as well as saturated or unsaturated.

All hydrocarbon residues for purposes of the invention can in principle be acyclic or cyclic, substituted or unsubstituted, branched or unbranched, as well as saturated or unsaturated. The hydrocarbon residues for purposes of the invention can in principle comprise heteroatoms, for example nitrogen, oxygen, or sulfur atoms. Acyclic, unbranched hydrocarbon residues that optionally can be substituted are respectively preferred with regard to $R^5$, $R^6$, and $R^7$. Suitable substituents are, for example, hydroxy, alkoxy, amino, or halogen groups.

The term "employ" is to be understood here in the broadest sense, i.e. a 1-aza-3,7-dioxabicyclo[3.3.0]octane compound of the general formula (I) is employed in order to degrade the aforesaid malodorants. "Degradation" of malodorants extends beyond merely masking off-odors, and means deactivation of the substances triggering the off-odor. "Deactivation" means here that the off-odor is at least diminished and in particular in fact entirely eliminated, i.e. extinguished. Whenever an off-odor is present, there must be an object from which that off-odor is proceeding, or a space or system in which the off-odor is perceptible. According to the present invention, a 1-aza-3,7-dioxabicyclo[3.3.0]octane compound of the general formula (I) can be delivered onto to that object or into that space or system in order to degrade the undesired odor. Delivery of the 1-aza-3,7-dioxabicyclo[3.3.0]octane compound of the general formula (I) can be accomplished, for example, by spraying or in the context of a washing or cleaning process.

The 1-aza-3,7-dioxabicyclo[3.3.0]octane compound of the general formula (I) can, for example, be sprayed into the room air; it can, for example, be placed into a container with water or with a washing bath; it can be delivered directly onto any demarcated object, for example including a sweaty shirt, or onto a plurality of such objects, for example a laundry load made up of many dirty shirts or the like. It has been found, surprisingly, that the method according to the present invention makes possible an appreciable degradation, to the point of extinction, of off-odors.

The method according to the present invention is successfully usable in particular in order to minimize or extinguish off-odors with regard to bad-smelling textiles that result, for example, after sporting activity, or with regard to off-odors in the toilet or WC sector.

It is presumed on the part of the inventors that the functional principle of the 1-aza-3,7-dioxabicyclo[3.3.0]octane compound that is used in off-odor elimination is also based on the fact that this aforesaid compound releases by hydrolysis not only fragrance aldehydes and/or fragrance ketones but also amino alcohols, thereby enabling deactivation of malodorants. It has been discovered, however, surprisingly, that the 1-aza-3,7-dioxabicyclo[3.3.0]octane compounds of the general formula (I) that are employed make possible better off-odor elimination that the otherwise comparable combination of separately employed amino alcohols and fragrances, i.e. fragrance aldehydes and/or fragrance ketones, i.e. the breakdown products of the 1-aza-3,7-dioxabicyclo[3.3.0]octane compound. Better off-odor elimination as compared with individually employed amino alcohol or fragrance is in any case achieved. The superior effect has also been found in particular for applications in the washing machine. The release of fragrance aldehydes or fragrance ketones and amino alcohols by hydrolysis is particularly advantageous, for example, in the case of perspiration, with the result that the bad odor that forms can be intercepted directly as it is produced.

It has proven to be particularly advantageous, in the context of counteracting off-odors for purposes of the invention, to carry out the method according to the present invention in the presence of catalytic quantities of acids, preferably Lewis and/or Brønsted acids, in particular Brønsted acids.

Even catalytic quantities of water, resulting e.g. from usual atmospheric moisture or ambient air, are sufficient to ensure particularly efficient degradation of the effect of malodorants as defined by the invention.

The influence of ambient air is also favorable for purposes of the invention because said air is as a rule slightly acidic. The reason for this is that carbon dioxide is in part dissolved in atmospheric moisture, i.e. in the water present in air, and is always present in the air; this forms (in formal terms) carbonic acid, so that the $H^+$ ion concentration of that moisture rises. Catalytic quantities of acids are thus as a rule contained in ambient air and in the atmospheric moisture contained therein.

As has already been made clear, in formula (I) the residues $R^1$, $R^2$, $R^3$, $R^4$ mutually independently denote residues that, in a compound of the general formula $R^1$—C(═O)—$R^2$ or $R^3$—C(═O)—$R^4$, yield a fragrance aldehyde having at least six carbon atoms or a fragrance ketone having at least six carbon atoms.

Preferably, residues $R^1$ and $R^2$ or $R^3$ and $R^4$ that yield a fragrance ketone in a compound of the general formula $R^1$—C(═O)—$R^2$ or $R^3$—C(═O)—$R^4$ are present in at most one of the structural elements —$CR^1R^2$ or —$CR^3R^4$. In particular, residues $R^1$ and $R^2$ as well as $R^3$ and $R^4$ that respectively yield a fragrance aldehyde, in particular the same fragrance aldehyde, in a compound of the general formula $R^1$—C(═O)—$R^2$ or $R^3$—C(═O)—$R^4$ are present in both structural elements —$CR^1R^2$ and —$CR^3R^4$.

According to a preferred embodiment of the invention, the fragrance aldehyde is selected from adoxal (2,6,10-trimethyl-9-undecenal), anisaldehyde (4-methoxybenzaldehyde), cymal (3-(4-isopropylphenyl)-2-methylpropanal), ethyl vanillin, florhydral (3-(3-isopropylphenyl)butanal), helional (3-(3,4-methylenedioxyphenyl)-2-methylpropanal), heliotropin, hydroxycitronellal, lauraldehyde, lyral (3- and 4-(4-hydroxy-4-methyl pentyl)-3-cyclohexene-1-carboxaldehyde), methyl nonyl acetaldehyde, lilial (3-(4-tert-butylphenyl)-2-methylpropanal), phenyl acetaldehyde, undecylenealdehyde, vanillin, 2,6,10-trimethyl-9-undecenal, 3-dodecen-1-al, alpha-n-amylcinnamaldehyde, melonal (2,6-dimethyl-5-heptenal), 2,4-dimethyl-3-cyclohexene-1-carboxaldehyde (triplal), 4-methoxybenzaldehyde, benzaldehyde, 3-(4-tert-butylphenyl)propanal, 2-methyl-3-(para-methoxyphenyl)propanal, 2-methyl-4-(2,6,6-trimethyl-2(1)-cyclohexen-1-yl)butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzylaldehyde, 1,2,3,4,5,6,7,8-octahydro-8,8-dimethyl-2-naphthaldehyde, 2,4-dimethyl-3-cyclohexene-1-carboxaldehyde, 2-methyl-3-(isopropylphenyl)propanal, 1-decanal, 2,6-dimethyl-5-heptenal, 4-(tricyclo[5.2.1.0(2,6)]-decylidene-8)-butanal, octahydro-4,7-methane-1H-indenecarboxaldehyde, 3-ethoxy-4-hydroxybenzaldehyde, para-ethyl-alpha,alpha-dimethylhydrocinnamaldehyde, alpha-methyl-3,4-(methylenedioxy)hydrocinnamaldehyde, 3,4-methylenedioxybenzaldehyde, alpha-n-hexylcinnamaldehyde, m-cymene-7-carboxaldehyde, alpha-methyl phenyl acetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3-cyclohexenecarboxaldehyde, 1-dodecanal, 2,4-dimethylcyclohexene-3-carboxaldehyde, 4-(4-hydroxy-4-methyl pentyl)-3-cylohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tert-butyl)propanal, dihydrocinnamaldehyde, 1-methyl-4-(4-methyl-3-pentenyl)-3-cyclohexene-1-carboxaldehyde, 5- or 6-methoxyhexahydro-4,7-methane indane-1- or -2-carboxaldehyde, 3,7-dimethyloctan-1-al, 1-undecanal, 10-undecen-1-al, 4-hydroxy-3-methoxybenzaldehyde, 1-methyl-3-(4-methylpentyl)-3-cyclohexenecarboxaldehyde, 7-hydroxy-3,7-dimethyloctanal, trans-4-decenal, 2,6-nonadienal, para-tolylacetaldehyde, 4-methyl phenyl acetaldehyde, 2-methyl-4-(2,6,6-trimethyl-1-cyclohexen-1-yl)-2-butenal, ortho-methoxycinnamaldehyde, 3,5,6-trimethyl-3-cyclohexenecarboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methane indane-1-carboxaldehyde, 2-methyloctanal, alpha-methyl-4-(1-methyl ethyl)benzeneacetaldehyde, 6,6-dimethyl-2-norpinene-2-propionaldehyde, para-methyl phenoxy acetaldehyde, 2-methyl-3-phenyl-2-propen-1-al, 3,5,5-trimethylhexanal, hexahydro-8,8-dimethyl-2-naphthaldehyde, 3-propylbicyclo[2.2.1]-hept-5-ene-2-carbaldehyde, 9-decenal, 3-methyl-5-phenyl-1-pentanal, methyl nonyl acetaldehyde, hexanal, and trans-2-hexenal.

According to a preferred embodiment of the invention, the fragrance ketone is selected from methyl beta-naphthyl ketone, musk indanone (1,2,3,5,6,7-hexahydro-1,1,2,3,3-pentamethyl-4H-inden-4-one), tonalide (6-acetyl-1,1,2,4,4,7-hexamethyltetraline), alpha-damascone, beta-damascene, delta-damascone, isodamascone, damascenone, methyl dihydrojasmonate, menthone, carvone, camphor, koavone (3,4,5,6,6-pentamethylhept-3-en-2-one), fenchone, alpha-ionone, beta-ionone, gamma-methyl ionone, fleuramone (2-heptylcyclopentanone), dihydrojasmone, cis-jasmon, iso-E-super (1-(1,2,3,4,5,6,7,8-octahydro-2,3,8,8-tetramethyl-2-naphthalenyl)-ethan-1-one (and isomers)), methyl cedrenyl ketone, acetophenone, methyl acetophenone, para-methoxyacetophenone, methyl beta-naphthyl ketone, benzylacetone, benzophenone, para-hydroxyphenyl butanone, celery ketone (3-methyl-5-propyl-2-cyclohexenone), 6-isopropyldecahydro-2-naphthone, dimethyl octenone, Frescomenthe (2-butan-2-yl-cyclohexan-1-one), 4-(1-ethoxyvinyl)-3,3,5,5-tetramethylcyclohexanone, methyl heptenone, 2-(2-(4-methyl-3-cyclohexen-1-yl)propyl)cyclopentanone, 1-(p-menthen-6(2)yl)-1-propanone, 4-(4-hydroxy-3-methoxyphenyl)-2-butanone, 2-acetyl-3,3-dimethylnorbornane, 6,7-dihydro-1,1,2,3,3-pentamethyl-4(5H)-indanone, 4-damascol, dulcinyl (4-(1,3-benzodioxol-5-yl)butan-2-one), hexalone (1-(2,6,6-trimethyl-2-cyclohexen-1-yl)-1,6-heptadien-3-one), isocyclemone E (2-acetonaphthone-1,2,3,4,5,6,7,8-octahydro-2,3,8,8-tetramethyl), methyl nonyl ketone, methyl cyclocitrone, methyl lavender ketone, orivone (4-tert-amyl cyclohexanone), 4-tert-butyl cyclohexanone, delphone (2-pentylcyclopentanone), muscone (CAS 541-91-3), neobutenone (1-(5,5-dimethyl-1-cyclohexenyl)pent-4-en-1-one), plicatone (CAS 41724-19-0), veloutone (2,2,5-trimethyl-5-pentylcyclopentan-1-one), 2,4,4,7-tetramethyloct-6-en-3-one, and tetrameran (6,10-dimethylundecen-2-one).

According to a preferred embodiment of the invention, $R^5$ and $R^7$ mutually independently each advantageously denote hydrogen or a $C_{1-6}$ hydrocarbon residue that can optionally be substituted, preferably a $C_{1-3}$ hydrocarbon residue. Particularly preferably $R^5$ and $R^6$ are each hydrogen or each a methyl or ethyl residue, but in particular are each hydrogen.

According to a preferred embodiment of the invention, $R^1$ and $R^3$ mutually independently each advantageously denote a $C_{6-24}$ hydrocarbon residue, preferably a $C_{7-24}$ hydrocarbon residue, where the hydrocarbon residue can be acyclic or cyclic, substituted or unsubstituted, branched or unbranched, as well as saturated or unsaturated.

In a further preferred embodiment, $R^2$, $R^4$, $R^5$, $R^7$ denote hydrogen, $R^1$ and $R^3$ each denote a $C_{6-24}$ hydrocarbon residue, preferably a $C_{7-24}$ hydrocarbon residue, where the hydrocarbon residue can be acyclic or cyclic, substituted or unsubstituted, branched or unbranched, as well as saturated or unsaturated, and $R^6$ denotes hydrogen or $C_{1-24}$ hydrocarbon residue that can be acyclic or cyclic, substituted or unsubstituted, branched or unbranched, as well as saturated or unsaturated, and that in particular can be substituted with one or two hydroxyl groups and/or an amino group, where up to 8 non-adjacent —$CH_2$ groups can also be replaced with —O—.

With reference to $R^6$, preferred residues are $C_{1-16}$ hydrocarbon residues, in particular $C_{1-12}$ hydrocarbon residues, more preferably $C_{1-6}$ hydrocarbon residues, most preferably $C_{1-3}$ hydrocarbon residues. These are preferably unbranched, acyclic alkyl residues. They can also be substituted. They can also be, for example, mono- or dihydroxyalkyl residues that can also have an amino group instead of or in addition to the hydroxyl groups. If the hydrocarbon residues are interrupted by —O—, these are preferably structures of the formulas —$CH_2$—$CH_2$—O— or —$CH_2$—$CH(CH_3)$—O—. Such compounds are easily accessibly by alkoxylation of the corresponding hydroxyl compounds. Very particularly preferred residues $R^6$ are methyl, ethyl, or hydroxymethyl residues, or hydrogen.

If, in the 1-aza-3,7-dioxabicyclo[3.3.0]octane compound of the general formula (I), the residues $R^2$ and $R^4$ each denote hydrogen, a preferred embodiment of the invention then exists.

If, in the 1-aza-3,7-dioxabicyclo[3.3.0]octane compound of the general formula (I), the residues $R^2$, $R^4$, $R^5$, $R^7$ each denote hydrogen, and the residue $R^6$ denotes a methyl, ethyl, or hydroxymethyl residue or hydrogen, and the residues $R^1$ and $R^3$ mutually independently each denote a $C_{6-24}$ hydrocarbon residue, preferably a $C_{7-24}$ hydrocarbon residue, where the hydrocarbon residue can be acyclic or cyclic, substituted or unsubstituted, branched or unbranched, as well as saturated or unsaturated, a further preferred embodiment of the invention then exists.

Suitable oxazolidines in accordance with the general formula (I) are therefore, for example, 1-aza-3,7-dioxa-2,8-diheptylbicyclo[3.3.0]octane, 1-aza-3,7-dioxa-2,8-diheptyl-5-methylbicyclo[3.3.0]octane, 1-aza-3,7-dioxa-2,8-diheptyl-5-hydroxymethylbicyclo[3.3.0]octane, 1-aza-3,7-dioxa-2,8-diheptyl-5-ethylbicyclo[3.3.0]octane, 1-aza-3,7-dioxa-2,8-dioctylbicyclo[3.3.0]octane, 1-aza-3,7-dioxa-2,8-dioctyl-5-methylbicyclo[3.3.0]octane, 1-aza-3,7-dioxa-2,8-dioctyl-5-hydroxymethylbicyclo[3.3.0]octane, and 1-aza-3,7-dioxa-2,8-dioctyl-5-ethylbicyclo[3.3.0]octane.

The compounds of the general formula (I) that are usable according to the present invention are obtainable in particular by reacting compounds of the general formula (II)

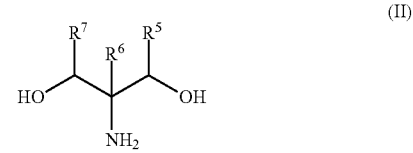

with compounds of the general formulas $R^1$—C(=O)—$R^2$ and $R^3$—C(=O)—$R^4$ accompanied by ring closure. A suitable substance according to formula (II) is, for example, 2-aminopropane-1,3-diol. The statements already made above apply respectively regarding the residues $R^1$ to $R^6$. For purposes of the invention, the general formulas $R^1$—C(=O)—$R^2$ and $R^3$—C(=O)—$R^4$ very generally represent fragrance aldehydes or fragrance ketones. Fragrance aldehydes are those fragrances that are chemically an aldehyde and that advantageously produce in humans an, in particular, pleasant olfactory sensation. Fragrance ketones are those fragrances that are chemically a ketone and that advantageously produce in humans an, in particular, pleasant olfactory sensation. Particularly suitable fragrance aldehydes and fragrance ketones are listed by way of example above. Two examples may be given for illustration. In the fragrance aldehyde octanal, for example, according to the general formula $R^1$—C(=O)—$R^2$ the residue $R^1$ denotes a heptyl residue (i.e. $CH_3$—$(CH_2)_6$—) and the residue $R^2$ denotes hydrogen, or vice versa. In the case of the fragrance ketone methyl nonyl ketone, for example, according to the general formula $R^1$—C(=O)—$R^2$ the residue $R^1$ denotes a methyl residue and the residue $R^2$ denotes a nonyl residue (i.e. $CH_3$—$(CH_2)_8$—), or vice versa.

In principle it is possible to use as fragrance aldehydes and/or fragrance ketones all usual fragrance aldehydes and/or fragrance ketones that are employed in particular to bring about a pleasant olfactory sensation in humans. Fragrance aldehydes and/or fragrance ketones of this kind are known to one skilled in the art and are also described in the patent literature, for example in US 2003/0158079 A1, paragraphs [0154] and [0155].

In order to manufacture the compounds of the general formula (I) that are to be employed according to the present invention, it is thus possible to react a compound of the general formula (II) with aldehydes, ketones, or mixtures of ketone and aldehydes, accompanied by ring closure. According to a preferred embodiment of the invention, the compounds of the general formula (I) are derived from one molecule of the general formula (II) and two aldehyde molecules, which can the same or different, or from one aldehyde molecule and one ketone molecule. Monocyclic compounds are also present in the product mixture when less-than-stoichometric quantities of aldehydes and/or ketones are reacted. The proportion of bicyclic compounds to monocyclic compounds can, however, easily be adjusted by selecting the molar ratio between aldehyde/ketone and the compound of the general formula (II).

The reaction is carried out preferably in a suitable solvent or in situ. Suitable solvents are, for example, aromatic-containing hydrocarbons such as toluene. The reaction is carried out preferably at a temperature in the range from 80 to 150° C., particularly preferably 100 to 140° C. For example, the compound of the general formula (II) is made ready in the solvent under a nitrogen atmosphere together with the desired ketone and/or aldehyde. The reaction mixture is then heated. Heating is often performed under reflux on a water separator. The reaction product that is obtained is isolated using usual methods, and optionally purified. The manufacture of compounds of the general formula (I) is also described in detail with reference to synthesis examples in WO 2007/087977 A1, to which reference is hereby made.

In a preferred embodiment of the invention, the 1-aza-3,7-dioxabicyclo[3.3.0]octane compound of the general formula (I) is employed together with fragrances, where the 1-aza-3,7-dioxabicyclo[3.3.0]octane compound is employed in quantities by weight, in terms of the total quantity of fragrance, preferably in the range from 1:100 to 100:1, in particular from 10:1 to 1:50.

The further fragrances that can additionally be employed in the method according to the present invention are not subject to any particular limitations. Individual fragrance compounds of natural or synthetic origin, e.g of the ester, ether, aldehyde, ketone, alcohol, and hydrocarbon types, can thus be used. Fragrance compounds of the ester type are, for example, benzyl acetate, phenoxyethyl isobutyrate, p-tert-butyl cyclohexylacetate, linalyl acetate, dimethyl benzyl carbinyl acetate (DMBCA), phenyl ethyl acetate, benzyl acetate, ethyl methyl phenyl glycinate, allylcyclohexyl propionate, styrallyl propionate, benzyl salicylate, cyclohexyl salicylate, floramate, melusate, and jasmacyclate. Included among the ethers are, for example, benzyl ethyl ether and ambroxan; among the aldehydes, for example, the linear alkanals having 8 to 18 carbon atoms, citral, citronellal, citronellyloxyacetaldehyde, cyclamenaldehyde (3-(4-propan-2-ylphenyl)butanal), lilial, and bourgeonal; among the ketones, for example, ionones, α-isomethylionone and methyl cedryl ketone; among the alcohols, anethol, citronellol, eugenol, geraniol, linalool, phenyl ethyl alcohol, and terpineol; the hydrocarbons include principally terpenes such as limonene and pinene. Preferably, however, mixtures of different fragrances that together generate an attractive scent note are used.

Natural fragrance mixtures can also be employed, such as those accessible from plant sources, for example pine, citrus, jasmine, patchouli, rose, or ylang-ylang oil. Also suitable are muscatel sage oil, chamomile oil, clove oil, lemon balm oil, mint oil, cinnamon leaf oil, linden blossom oil, juniper berry oil, vetiver oil, olibanum oil, galbanum oil, and labdanum oil, as well as orange blossom oil, neroli oil, orange peel oil, and sandalwood oil.

Further conventional fragrances that can additionally be employed in the context of the present invention are, for example, the essential oils such as angelica oil, anise oil, arnica flower oil, basil oil, bay oil, champaca flower oil, silver fir oil, silver fir cone oil, elemi oil, eucalyptus oil, fennel oil, fir needle oil, galbanum oil, geranium oil, gingergrass oil, guaiac wood oil, balsam gurjun oil, helichrysum oil, ho oil, ginger oil, iris oil, cajeput oil, calamus oil, chamomile oil, camphor oil, kanaga oil, cardamom oil, cassia oil, pine needle oil, balsam copaiva oil, coriander oil, curled peppermint oil, caraway oil, cumin oil, lavender oil, lemon grass oil, lime oil, tangerine oil, lemon balm oil, ambrette seed oil, myrrh oil, clove oil, neroli oil, niaouli oil, olibanum oil, oregano oil, palmarosa oil, patchouli oil, balsam peru oil, petitgrain oil, pepper oil, peppermint oil, pimento oil, pine oil, rose oil, rosemary oil, sandalwood oil, celery oil, spik oil, star anise oil, turpentine oil, thuja oil, thyme oil, verbena oil, vetiver oil, juniper berry oil, wormwood oil, wintergreen oil, ylang-ylang oil, hyssop oil, cinnamon oil, cinnamon leaf oil, citronella oil, citron oil, and cypress oil, as well as ambrettolide, α-amylcinnamaldehyde, anethole, anisealdehyde, anise alcohol, anisole, anthranilic acid methyl ester, acetophenone, benzyl acetone, benzaldehyde, benzoic acid ethyl ester, benzophenone, benzyl alcohol, benzyl acetate, benzyl benzoate, benzyl formate, benzyl valerate, borneol, bornyl acetate, boisambrene forte, α-bromostyrene, n-decylaldehyde, n-dodecylaldehyde, eugenol, eugenol methyl ether, eucalyptol, farnesol, fenchone, fenchyl acetate, geranyl acetate, geranyl formate, heliotropin, heptyne carboxylic acid methyl ester, heptaldehyde, hydroquinone dimethyl ether, hydroxycinnamaldehyde, hydroxycinnamyl alcohol, indole, irone, isoeugenol, isoeugenol methyl ether, isosafrol, jasmone, camphor, carvacrol, carvone, p-cresol methyl ether, coumarin, p-methoxyacetophenone, methyl n-amyl ketone, methylanthranilic acid methyl ester, p-methylacetophenone, methylchavicol, p-methylquinoline, methyl β-naphthyl ketone, methyl-n-nonylacetaldehyde, methyl n-nonyl ketone, muscone, β-naphthol ethyl ether, β-naphthol methyl ether, nerol, n-nonylaldehyde, nonyl alcohol, n-octylaldehyde, p-oxyacetophenone, pentadecanolide, β-phenyl ethyl alcohol, phenylacetic acid, pulegone, safrole, salicylic acid isoamyl ester, salicylic acid methyl ester, salicylic acid hexyl ester, salicylic acid cyclohexyl ester, santalol, sandelice, skatole, terpineol, thymene, thymol, troenan, γ-undelactone, vanillin, veratrumaldehyde, cinnamaldehyde, cinnamyl alcohol, cinnamic acid, cinnamic acid ethyl ester, cinnamic acid benzyl ester, diphenyl oxide, limonene, linalool, linalyl acetate and propionate, melusate, menthol, menthone, methyl-n-heptenone, pinene, phenylacetaldehyde, terpinyl acetate, citral, citronellal, and mixtures thereof.

According to a preferred embodiment of the invention, the method according to the present invention is directed toward the degradation of malodorants on hard and/or soft surfaces.

If the method according to the present invention relates to the degradation of off-odors on textiles in the context of a textile treatment method in which the textile is exposed, in a manual or automatic washing or soaking process, to an aqueous washing bath that contains a 1-aza-3,7-dioxabicyclo[3.3.0]octane compound of the general formula (I), where the temperature of the washing bath is 5 to 95° C., preferably 10 to 60° C., and in particular 15 to 40° C., a preferred embodiment of the invention then also exists. The 1-aza-3,7-dioxabicyclo[3.3.0]octane compound of the general formula (I) is employed in this context in particular as a constituent of a (preferably fragrance-containing) washing, cleaning, or care-providing agent. A particularly good decrease in the bad odor occurs in this context. The treatment duration is preferably within a time period from 1 to 120 minutes, for example in the range from 5 to 60 minutes, in particular from 15 to 45 minutes. The concentration of the 1-aza-3,7-dioxabicyclo[3.3.0]octane compound of the general formula (I) in the aqueous treatment bath is preferably in the range from 0.0004 to 0.12 g/L, in particular from 0.002 to 0.04 g/L.

According to a further preferred embodiment of the invention, the method according to the present invention relates to a method for degrading off-odors on textiles, in which method a liquid containing a 1-aza-3,7-dioxabicyclo[3.3.0]octane compound of the general formula (I) is sprayed onto the textile. If application is accomplished in this context by means of a spray can (pressurized gas can, pressurized gas package, aerosol package) or a pump atomizer to be operated mechanically (pump spray), forming a spray mist, foam, a paste, or liquid stream, a preferred embodiment of the invention again exists.

The method according to the present invention is in principle equally suitable for off-odor degradation in the context of textile treatment and for the cleaning of hard surfaces (e.g. floors), as well as for cosmetic use and in the air care sector and in air freshening.

A method for degrading off-odors on hard surfaces, in which method the hard surface is brought into contact with a (preferably aqueous) liquid containing a 1-aza-3,7-dioxabicyclo[3.3.0]octane compound of the general formula (I), in particular by rinsing and/or spraying, accordingly corresponds to a further preferred embodiment of the invention.

A method for degrading off-odors in room air, in particular in living rooms, kitchens, bathrooms, toilet areas, closets, and automobiles, employing a 1-aza-3,7-dioxabicyclo[3.3.0]octane compound of the general formula (I), likewise corresponds to a preferred embodiment of the invention. A method in which the 1-aza-3,7-dioxabicyclo[3.3.0]octane compound of the general formula (I) is introduced into the room air via sticks, cards, blocks, or spray is particularly preferred.

Also preferred in this connection is a method in which release of the 1-aza-3,7-dioxabicyclo[3.3.0]octane compound of the general formula (I) occurs via a toilet flush cleaner for suspension in the toilet bowl.

It is preferred in general to embody the method according to the present invention in such a way that the 1-aza-3,7-dioxabicyclo[3.3.0]octane compound of the general formula (I) is employed together with fragrances. A preferred embodiment of the invention correspondingly exists when, in a method according to the present invention, the 1-aza-3,7-dioxabicyclo[3.3.0]octane compound of the general formula (I) is employed together with fragrances, where the 1-aza-3,7-dioxabicyclo[3.3.0]octane compound is employed in weight quantities, based on the total fragrance quantity, preferably in the range from 1:100 to 100:1, in particular from 10:1 to 1:50.

According to the present invention a washing, cleaning, or care-providing agent containing a 1-aza-3,7-dioxabicyclo[3.3.0]octane compound of the general formula (I) usable according to the present invention can be employed preferably in quantities from 0.0001 to 5 wt %, "wt %" being based on the total agent, to degrade off-odors.

Washing, cleaning, or care-providing agents (hereinafter called "washing or cleaning agents") usable according to the present invention preferably contain, besides the 1-aza-3,7-dioxabicyclo[3.3.0]octane compound of the general formula (I), at least one, preferably several active components, in particular components having washing, care-providing, and/or cleaning activity, advantageously selected from the group comprising anionic surfactants, cationic surfactants, amphoteric surfactants, nonionic surfactants, acidifying agents, alkalizing agents, anticrease compounds, antibacterial substances, antioxidants, antiredeposition agents, antistatic agents, builder substances (builders), bleaching agents, bleach activators, bleach stabilizers, bleach catalysts, ironing adjuvants, fragrances, shrinkage preventers, electrolytes, enzymes, color protectants, dyes, color transfer inhibitors, fluorescent agents, fungicides, germicides, odor-complexing substances, hydrotropes, rinse aids, complexing agents, preservatives, corrosion inhibitors, optical brighteners, luster agents, pH adjusting agents, proofing and impregnation agents, polymers, swelling and anti-slip agents, foam inhibitors, sheet silicates, dirt-repelling substances, silver protectants, silicone oils, UV protection substances, viscosity regulators, thickening agents, discoloration inhibitors, anti-gray agents, vitamins, and/or avivage active agents.

The quantities of the further possible ingredients in the washing or cleaning agents usable according to the present invention are based on the respective intended application of the relevant agents, and one skilled in the art is familiar in principle with the orders of magnitude of the quantities of optional ingredients to be used, or can gather them from the relevant technical literature.

For example, the surfactant content selected will be higher or lower depending on the intended application of the washing or cleaning agents usable according to the present invention. For example, the surfactant content of, for example, washing agents is usually between, for example, 5 and 50 wt %, preferably between 10 and 30 wt %, and in particular between 15 and 25 wt %, while cleaning agents for automatic dishwashing usually contain between, for example, 0.1 and 10 wt %, preferably between 0.5 and 7.5 wt %, and in particular between 1 and 5 wt % surfactants.

The washing or cleaning agents usable according to the present invention can preferably contain surfactants; appropriate surfactants are in particular anionic surfactants, nonionic surfactants, and mixtures thereof, but also cationic surfactants.

Among the optionally usable nonionic surfactants are the alkoxylates, in particular ethoxylates and/or propoxylates, of saturated or mono- to polyunsaturated linear or branched-chain alcohols having 10 to 22 carbon atoms, preferably 12 to 18 carbon atoms. The degree of alkoxylation of the alcohols is as a rule between 1 and 20, preferably between 3 and 10. They can be manufactured, in known fashion, by reacting the corresponding alcohols with the corresponding alkylene oxides. The derivatives of fatty alcohols are particularly suitable, although their branched-chain isomers, in particular so-called oxo alcohols, can also be used to manufacture usable alkoxylates. The alkoxylates, in particular the ethoxylates, of primary alcohols having linear, in particular dodecyl, tetradecyl, hexadecyl, or octadecyl residues, as well as mixtures thereof, are accordingly usable. Also usable are corresponding alkoxylation products of alkylamines, of vicinal diols, and of carboxylic acid amides that correspond to the aforesaid alcohols in terms of the alkyl portion. Additionally suitable are the ethylene-oxide and/or propylene-oxide insertion products of fatty acid alkyl esters, as well as fatty acid polyhydroxyamides.

So-called alkylpolyglycosides suitable for optional incorporation into the agents usable according to the present invention are compounds of the general formula $(G)_n$-$OR^8$, in which $R^8$ signifies an alkyl or alkenyl residue having 8 to 22 carbon atoms, G a glycose unit, and n a number between 1 and 10. The glycoside component $(G)_n$ refers to oligomers or polymers from naturally occurring aldose or ketose monomers, among which are included, in particular, glucose, mannose, fructose, galactose, talose, gulose, altrose, allose, idose, ribose, arabinose, xylose, and lyxose. The oligomers made up of glycosidically linked monomers of this kind are characterized not only by the nature of the sugars contained in them but also by their number (the so-called degree of oligomerization). The degree of oligomerization n, constituting a magnitude to be ascertained analytically, generally assumes fractional numerical values; its value is between 1 and 10, for the glycosides preferably used, below a value of 1.5, in particular between 1.2 and 1.4. Because of its good availability, glucose is a preferred monomer module. The alkyl or alkenyl portion $R^8$ of the glycosides preferably likewise derives from easily accessible derivatives of renewable raw materials, in particular from fatty alcohols, although their branched-chain isomers, in particular so-called oxo alcohols, can also be used to manufacture usable glycosides. The primary alcohols having linear octyl, decyl, dodecyl, tetradecyl, hexadecyl, or octadecyl residues, as well as mixtures thereof, are accordingly usable in particular. Particularly preferred alkylglycosides contain a coconut oil alkyl residue, i.e. mixtures where substantially $R^8$=dodecyl and $R^8$=tetradecyl.

Nonionic surfactant is optionally contained in washing or cleaning agents usable according to the present invention preferably in quantities from 0.1 wt % to 30 wt %, in particular from 1 wt % to 25 wt %, "wt %" being based on the total washing or cleaning agent.

The washing or cleaning agents can instead or additionally contain further optional surfactants, preferably anionic surfactants.

Anionic surfactants of the sulfate or sulfonate type are preferably optionally contained, in quantities preferably not above 30 wt %, in particular from 0.1 wt % to 18 wt %, based in each case on the total washing or cleaning agent. Anionic surfactants particularly suitable for use in the washing or cleaning agents according to the present invention are alkyl and/or alkenyl sulfates, having 8 to 22 carbon atoms, which carry an alkali-, ammonium-, or alkyl- or hydroxyalkyl-substituted ammonium ion as counter-cation. The derivatives of fatty alcohols having, in particular, 12 to 18 carbon atoms, and their branched-chain analogs (the so-called oxo alcohols), are preferred. The alkyl and alkenyl sulfates can be manufactured in known fashion by reacting the corresponding alcohol component with a usual sulfating reagent, in particular sulfur trioxide or chlorosulfonic acid, followed by neutralization with alkali-, ammonium-, or alkyl- or hydroxyalkyl-substituted ammonium bases. Such alkyl and/or alkenyl sulfates are optionally contained in the washing or cleaning agents preferably in quantities from 0.1 wt % to 20 wt %, in particular from 0.5 wt % to 18 wt %.

Also included among the usable surfactants of the sulfate type are sulfated alkoxylation products of the aforesaid alcohols (so-called ether sulfates). Such ether sulfates contain preferably 2 to 30, in particular 4 to 10 ethylene glycol groups per molecule. Included among the usable anionic surfactants of the sulfonate type are the α-sulfo esters obtainable by reacting fatty acid esters with sulfur trioxide and subsequent neutralization, in particular the sulfonation products deriving from fatty acids having 8 to 22 carbon atoms, preferably 12 to 18 carbon atoms, and linear alcohols having 1 to 6 carbon atoms, preferably 1 to 4 carbon atoms, and the sulfofatty acids proceeding therefrom by formal saponification.

Anionic surfactants optionally usable with particular preference are alkylbenzenesulfonates, such as e.g. sodium dodecylbenzenesulfonate.

Anionic surfactant is optionally contained in washing or cleaning agents according to the present invention preferably in quantities from 0.1 wt % to 30 wt %, in particular from 1 wt % to 25 wt %, "wt %" being based on the total washing or cleaning agent.

Further appropriate surfactant ingredients of the washing or cleaning agents usable according to the present invention are soaps; saturated fatty acid soaps such as the salts of lauric acid, myristic acid, palmitic acid, or stearic acid, as well as soaps derived from natural fatty acid mixtures, for example coconut, palm-kernel, or tallow fatty acids, are suitable. Those soap mixtures that are made up of 50 to 100 wt % saturated $C_{12}$ to $C_{18}$ fatty acid soaps and up to 50 wt % oleic acid soap are particularly preferred. Soap is optionally contained in the washing or cleaning agents according to the present invention preferably in quantities from 0.1 wt % to 5 wt %. Larger quantities of soap (up to 20 wt %) can, however, also be optionally contained in particular in liquid washing or cleaning agents.

Cationic surfactants can also be optionally contained in the washing or cleaning agents usable according to the present invention. Examples of cationic surfactants are quaternary ammonium compounds having preferably one or, in particular, two hydrophobic alkyl residues. Esterquats are particularly preferred, i.e. quaternary ammonium compounds having two hydrophobic residues that each contain an ester group as a "defined break point" for easier biodegradability. Esterquats preferred for use are methyl-N-(2- hydroxyethyl)-N,N-di(tallowacyloxyethyl)ammonium methosulfate, bis-(palmitoyloxyethyl)hydroxyethylmethyl-ammonium methosulfate, 1,2-bis-[tallowacyloxy]-3-trimethylammonium propane chloride, N,N-dimethyl-N,N-di(tallowacyloxyethyl)ammonium methosulfate, or methyl-N,N-bis(stearoyloxyethyl)-N-(2-hydroxyethyl)ammonium methosulfate.

The cationic surfactants are contained in the agents according to the present invention optionally in quantities preferably from 0.05 to 20 wt %, based on the total washing or cleaning agent. Quantities from 0.1 to 5 wt % are particularly preferred.

According to a preferred embodiment of the invention, surfactants are contained in washing or cleaning agents usable according to the present invention in a total quantity preferably from 5 to 50 wt %, in particular from 8 to 30 wt %. In laundry post-treatment agents in particular, preferably up to 30 wt %, in particular 5 to 15 wt % surfactants are used, among them preferably cationic surfactants at least in part.

A washing or cleaning agent usable according to the present invention can preferably contain at least one builder, preferably a water-soluble and/or water-insoluble, organic and/or inorganic builder. The use of water-soluble builders is preferred.

Included among the water-soluble organic builder substances are polycarboxylic acids, in particular citric acid and sugar acids, monomeric and polymeric aminopolycarboxylic acids, in particular methylglycinediacetic acid, nitrilotriacetic acid, and ethylenediaminetetraacetic acid, as well as polyaspartic acid, polyphosphonic acids, in particular aminotris(methylenephosphonic acid), ethylenediaminetetrakis(methylenephosphonic acid), and 1-hydroxyethane-1,1-diphosphonic acid, polymeric hydroxy compounds such as dextrin, as well as polymeric (poly)carboxylic acids, polymeric acrylic acids, methacrylic acids, maleic acids, and mixed polymers thereof, which can also contain, polymerized into them, small proportions of polymerizable substances having no carboxylic-acid functionality. Compounds of this class that are suitable although less preferred are copolymers of acrylic acid or methacrylic acid with vinyl ethers, such as vinyl methyl ethers, vinyl esters, ethylene, propylene, and styrene, in which the proportion of acid is at least 50 wt %.

Organic builder substances can be contained, if desired, in the washing or cleaning agents according to the present invention in quantities of up to 40 wt %, in particular up to 25 wt %, and preferably from 1 to 8 wt %. Quantities close to the aforesaid upper limit are used preferably in pasty or liquid, in particular water-containing, washing or cleaning agents according to the present invention. Washing or cleaning agents such as laundry post-treatment agents, for example fabric softeners, according to the present invention can also, if applicable, be free of organic builder.

Possibilities as water-soluble inorganic builder materials are, in particular, alkali silicates and polyphosphates, preferably sodium triphosphate. Crystalline or amorphous alkali aluminosilicates are optionally employed in particular as water-insoluble, water-dispersible inorganic builder materials, in quantities of e.g. up to 50 wt %, preferably not above 40 wt %, and in liquid agents in particular from 1 to 5 wt %, in the washing or cleaning agents according to the present invention. Among these, the crystalline sodium aluminosilicates of washing-agent quality, in particular zeolite A, P, and if applicable X, are preferred. Quantities close to the aforesaid upper limit are optionally used preferably in solid, particulate agents.

Suitable substitutes respectively partial substitutes for the aforesaid aluminosilicate are crystalline alkali silicates, which can be present alone or mixed with amorphous silicates. The alkali silicates usable in the washing or cleaning agents according to the present invention as builders preferably have a molar ratio of alkali oxide to $SiO_2$ below 0.95, in particular from 1:1.1 to 1:12, and can be present in amorphous or crystalline fashion. Amorphous alkali silicates are preferred.

It is also preferred for purposes of a further preferred embodiment to use at most small quantities of water-insoluble builder materials (such as e.g. zeolite), for example in quantities from 0 to 5 wt %, e.g. 0.1 to 2 wt %, based on the total washing or cleaning agent.

Builder substances are optionally contained in the washing or cleaning agents usable according to the present invention preferably in quantities of up to 60 wt %, in particular from 5 to 40 wt %. Laundry post-treatment agents, for example fabric softeners, according to the present invention are preferably free of inorganic builder.

Optionally usable peroxygen compounds that are suitable are, in particular, organic peracids respectively peracid salts of organic acids such as phthalimidopercapronic acid, perbenzoic acid, or salts of diperdodecanedioic acid, hydrogen peroxide, and inorganic salts that release hydrogen peroxide under utilization conditions, such as perborate, percarbonate, and/or persilicate. If solid peroxygen compounds are to be employed, they can be utilized in the form of powders or granulates, which in principle can also be encased in known fashion. Alkali percarbonate, alkali perborate monohydrate, or (in particular in liquid agents) hydrogen peroxide in the form of aqueous solutions that contain 3 wt % to 10 wt % hydrogen peroxide, can be used with particular preference. If a washing or cleaning agent according to the present invention contains bleaching agents, such as preferably peroxygen compounds, the latter are present in quantities of preferably up to 50 wt %, in particular from 5 wt % to 30 wt %. The optional addition of small quantities of known bleaching-agent stabilizers, for example phosphonates, borates particularly metaborates, and metasilicates, as well as magnesium salts such as magnesium sulfate, may be useful.

Compounds that, under perhydrolysis conditions, yield aliphatic peroxocarboxylic acids having preferably 1 to 10 carbon atoms, in particular 2 to 4 carbon atoms, and/or (optionally substituted) perbenzoic acid, can optionally be used as bleach activators. Substances that carry O- and/or N-acyl groups having the aforesaid number of carbon atoms, and/or optionally substituted benzoyl groups, are suitable. Multiply acylated alkylenediamines, in particular tetraacetylethylendiamine (TAED), acylated triazine derivatives, in particular 1,5-diacetyl-2,4-dioxohexahydro-1,3,5-triazine (DADHT), acylated glycolurils, in particular tetraacetyl glycoluril (TAGU), N-acylimides, in particular N-nonanoyl succinimide (NOSI), acylated phenolsulfonates, in particular n-nonanoyl or isononanoyl oxybenzenesulfonate (n- or iso-NOBS), carboxylic acid anhydrides, in particular phthalic acid anhydride, acylated polyvalent alcohols, in particular triacetin, ethylene glycol diacetate, 2,5-diacetoxy-2,5-dihydrofuran, and enol esters, as well as acetylated sorbitol and mannitol respectively mixtures thereof, acylated sugar derivatives, in particular pentaacetylglucose (PAG), pentaacetylfructose, tetraacetylxylose, and octaacetyllactose, as well as acetylated, optionally N-alkylated glutamine and gluconolactone, and/or N-acylated lactams, for example N-benzoylcaprolactam, are preferred. Hydrophilically substituted acyl acetates and acyl lactams are likewise preferably used. Combinations of conventional bleach activators can also be used. Such bleach activators can be contained in the usual quantity range, preferably in quantities from 1 to 10 wt %, in particular 2 to 8 wt %, based on the total agent.

Suitable enzymes optionally usable in the washing or cleaning agents usable according to the present invention are those from the class of the proteases, cutinases, amylases, pullulanases, hemicellulases, cellulases, lipases, oxidases, and peroxidases, as well as mixtures thereof. Enzymatic active agents recovered from fungi or bacteria, such as *Bacillus subtilis, Bacillus licheniformis, Streptomyces griseus, Humicola lanuginosa, Humicola insolens, Pseudomonas pseudoalcaligenes*, or *Pseudomonas cepacia*, are particularly suitable. The enzymes that are optionally used can be adsorbed onto carrier substances and/or embedded into encasing substances in order to protect them from premature inactivation. They are contained in the washing or cleaning agents usable according to the present invention preferably in quantities not above 5 wt %, in particular from 0.2 to 2 wt %.

The washing or cleaning agents can optionally contain as optical brighteners, for example, derivatives of diaminostilbenedisulfonic acid or alkali metal salts thereof. Suitable, for example, are salts of 4,4'-bis(2-anilino-4-morpholino-1,3,5-triazinyl-6-amino)stilbene-2,2'-disulfonic acid, or compounds of similar structure that carry, instead of the morpholino group, a diethanolamino group, a methylamino group, an anilino group, or a 2-methoxyethylamino group. Brighteners of the substituted diphenylstyryl type can also be present, for example the alkali salts of 4,4'-bis(2-sulfostyryl)diphenyl, of 4,4'-bis(4-chloro-3-sulfostyryl)diphenyl, or of 4-(4-chlorostyryl)-4'-(2-sulfostyryl)diphenyl. Mixtures of the aforesaid brighteners can also be used.

Included among the optionally usable foam inhibitors are, for example, organopolysiloxanes and mixtures thereof with microfine, optionally silanated silicic acid, as well as paraffin waxes and mixtures thereof with silanated silicic acid or bis-fatty acid alkylenediamides. Mixtures of different foam inhibitors, for example those made of silicones, paraffins, or waxes, can also be used with advantage. The optional foam inhibitors, in particular silicone- and/or paraffin-containing foam inhibitors, are preferably bound to a granular carrier substance that is soluble respectively dispersible in water. Mixtures of paraffins and bistearylethylenediamides are particularly preferred in this context.

In addition, the washing or cleaning agents usable according to the present invention can optionally also contain components that positively influence the ability of oils and fats to be washed out of textiles (so-called "soil release active agents"). This effect becomes particularly apparent when the soiled textile is one that has already been previously washed several times with a washing agent that contains this oil- and fat-releasing component. The preferred oil- and fat-releasing components include, for example, nonionic cellulose ethers such as methyl cellulose and methylhydroxypropyl cellulose having a 15 to 30 wt % proportion of methoxyl groups and a 1 to 15 wt % proportion of hydroxypropoxyl groups, based in each case on the nonionic cellulose ethers, as well as polymers, known from the existing art, of phthalic acid and/or terephthalic acid particularly of their derivatives with monomeric and/or polymeric diols, in particular polymers of ethylene terephthalates and/or polyethylene glycol terephthalates or anionically and/or nonionically modified derivatives thereof.

The washing or cleaning agents usable according to the present invention can optionally also contain color transfer inhibitors, preferably in quantities from 0.1 to 2 wt %, in particular 0.1 to 1 wt %, which in a preferred embodiment of the invention are polymers of vinylpyrrolidone, vinylimidazole, vinylpyridine-N-oxide, or copolymers thereof. Also usable are both polyvinylpyrrolidones, N-vinylimidazole/N-vinylpyrrolidone copolymers, polyvinyloxazolidones, copolymers based on vinyl monomers and carboxylic acid amides, pyrrolidone-group-containing polyesters and polyamides, grafted polyamidoamines and polyethylenimines, polymers having amide groups made up of secondary amines, polyamine-N-oxide polymers, polyvinyl alcohols, and copolymers based on acrylamidoalkenylsulfonic acids.

The optionally usable anti-gray agents have the ability to keep dirt that has been detached from the textile fibers suspended in the bath. Water-soluble colloids, usually organic in nature, are suitable for this, for example starch, size, gelatin, salts of ethercarboxylic or ethersulfonic acids of starch or of cellulose, or salts of acidic sulfuric-acid esters of cellulose or of starch. Water-soluble polyamides containing acid groups are also suitable for this purpose. Starch derivatives other than those recited above can also be used, for example aldehyde starches. Cellulose ethers such as carboxymethyl cellulose (sodium salt), methyl cellulose, hydroxyalkyl cellulose, and mixed ethers such as methylhydroxyethyl cellulose, methylhydroxypropyl cellulose, methylcarboxymethyl cellulose, and mixtures thereof can preferably be used, for example in quantities from 0.1 to 5 wt % based on the washing or cleaning agent usable according to the present invention, as optional anti-gray agents.

Included among the organic solvents optionally usable in the washing or cleaning agents usable according to the present invention, especially when the latter are present in liquid or pasty form, are alcohols having 1 to 4 carbon atoms, in particular methanol, ethanol, isopropanol, and tert-butanol, diols having 2 to 4 carbon atoms, in particular ethylene glycol and propylene glycol, as well as mixtures thereof, and the ethers derivable from the aforesaid compound classes. Water-miscible solvents of this kind can optionally be present in the washing or cleaning agents usable according to the present invention preferably in quantities not above 30 wt %, in particular from 6 to 20 wt %.

In order to establish a desired pH that does not result of itself from mixture of the other components, the washing or cleaning agents usable according to the present invention can optionally contain acids, in particular citric acid, acetic acid, tartaric acid, malic acid, lactic acid, glycolic acid, succinic acid, glutaric acid, and/or adipic acid, but also mineral acids, in particular sulfuric acid, or bases, in particular ammonium hydroxides or alkali hydroxides. pH regulators of this kind can optionally be contained in the washing or cleaning agents usable according to the present invention in quantities preferably not above 20 wt %, in particular from 1.2 to 17 wt %.

The manufacture of solid washing or cleaning agents usable according to the present invention can in principle be accomplished in known fashion, for example by spray-drying or granulation; an optional peroxygen compound and optional bleach catalyst are, if applicable, added later. A method comprising an extrusion step is preferred for the manufacture of washing or cleaning agents usable according to the present invention having an elevated bulk weight, in particular in the range from 650 g/l to 950 g/l. The manufacture of liquid washing or cleaning agents usable according to the present invention can likewise occur in a manner known per se.

A preferred washing or cleaning agent usable according to the present invention is a solid, in particular powdered washing agent that, besides the 1-aza-3,7-dioxabicyclo[3.3.0]octane compound of the general formula (I), can preferably contain components that are preferably selected from the following:
(a) anionic surfactants, such as preferably alkylbenzenesulfonate, alkyl sulfate, e.g. in quantities of preferably 5 to 30 wt %,
(b) nonionic surfactants, such as preferably fatty alcohol polyglycol ethers, alkylpolyglucoside, fatty acid glucamide, e.g. in quantities of preferably 0.5 to 15 wt %,
(c) builders, such as e.g. polycarboxylate, sodium citrate, in quantities from e.g. 0 to 70 wt %, advantageously 5 to 60 wt %, preferably 10 to 55 wt %, in particular 15 to 40 wt %,
(d) alkalis, such as e.g. sodium carbonate, in quantities from e.g. 0 to 35 wt %, advantageously 1 to 30 wt %, preferably 2 to 25 wt %, in particular 5 to 20 wt %,
(e) bleaching agents such as e.g. sodium perborate or sodium percarbonate, in quantities from e.g. 0 to 30 wt %, advantageously 5 to 25 wt %, preferably 10 to 20 wt %,
(f) corrosion inhibitors, e.g. sodium silicate, in quantities from e.g. 0 to 10 wt %, advantageously 1 to 6 wt %, preferably 2 to 5 wt %, in particular 3 to 4 wt %,
(g) stabilizers, e.g. phosphonates, advantageously 0 to 1 wt %,
(h) foam inhibitor, e.g. soap, silicone oils, paraffins, advantageously 0 to 4 wt %, preferably 0.1 to 3 wt %, in particular 0.2 to 1 wt %,
(i) enzymes, e.g. proteases, amylases, cellulases, lipases, advantageously 0 to 2 wt %, preferably 0.2 to 1 wt %, in particular 0.3 to 0.8 wt %,
(j) anti-gray agent, e.g. carboxymethyl cellulose, advantageously 0 to 1 wt %,
(k) discoloration inhibitor, e.g. polyvinylpyrrolidone derivatives, e.g. 0 to 2 wt %,
(l) adjusting agent, e.g. sodium sulfate, advantageously 0 to 20 wt %,
(m) optical brightener, e.g. stilbene derivative, biphenyl derivative, advantageously 0 to 0.4 wt %, in particular 0.1 to 0.3 wt %,
(n) optionally, further fragrances,
(o) optionally, water,
(p) optionally, soap,
(q) optionally, bleach activators,
(r) optionally, cellulose derivatives,
(s) optionally, soil repellents,
"wt %" being based in each case on the total agent.

In a further preferred embodiment, the washing or cleaning agent usable according to the present invention is solid, in particular particulate, and besides the 1-aza-3,7-dioxabicyclo[3.3.0]octane compound of the general formula (I) also contains 5 to 55 wt % builders, 2.5 to 20 wt % anionic surfactant, 1 to 20 wt % nonionic surfactant, 1 to 25 wt % bleaching agent, 0.5 to 8 wt % bleach activator, and 0.1 to 40 wt % adjusting agent, in particular alkali sulfate, as well as up to 2 wt %, in particular 0.4 to 1.2 wt % enzyme, preferably enzyme formulated in particulate form, in particular protease, lipase, amylase, cellulase, and/or oxidoreductase. This embodiment can optionally also be free of bleaching agent and bleach activator.

In another preferred embodiment of the invention, the washing or cleaning agent usable according to the present invention containing a 1-aza-3,7-dioxabicyclo[3.3.0]octane compound of the general formula (I) is present in liquid form, preferably in gel form. Preferred liquid washing or cleaning agents usable according to the present invention have water contents from e.g. 10 to 95 wt %, preferably 20 to 80 wt %, and in particular 30 to 70 wt %, based on the total agent. In the case of liquid concentrates the water content can also be particularly low, e.g. ≤30 wt %, preferably ≤20 wt %, in particular ≤15 wt %, for example 0.1 to 10 wt %, "wt %" being based in each case on the total agent. The liquid consumer products can also contain nonaqueous solvents.

A preferred washing or cleaning agent usable according to the present invention is a liquid, in particular gelled washing agent that, besides the 1-aza-3,7-dioxabicyclo[3.3.0]octane compound of the general formula (I), can preferably contain components that are preferably selected from the following:
anionic surfactants, such as preferably alkylbenzenesulfonate, alkyl sulfate, e.g. in quantities of preferably 5 to 40 wt %,
nonionic surfactants, such as preferably fatty alcohol polyglycol ethers, alkylpolyglucoside, fatty acid glucamide, e.g. in quantities of preferably 0.5 to 25 wt %,
builders, such as e.g. polycarboxylate, sodium citrate, advantageously 0 to 25 wt %, preferably 0.1 to 10 wt %, in particular 0.1 to 5 wt %,
foam inhibitor, e.g. silicone oils, paraffins, in quantities from e.g. 0 to 10 wt %, advantageously 0.1 to 4 wt %, preferably 0.2 to 2 wt %, in particular 1 to 3 wt %,
enzymes, e.g. proteases, amylases, cellulases, lipases, in quantities from e.g. 0 to 3 wt %, advantageously 0.1 to 2 wt %, preferably 0.2 to 1 wt %, in particular 0.3 to 0.8 wt %,
optical brightener, e.g. stilbene derivative, biphenyl derivative, in quantities from e.g. 0 to 1 wt %, advantageously 0.1 to 0.3 wt %, in particular 0.1 to 0.4 wt %,
optionally, further fragrances,
water,
optionally, soap, in quantities from e.g. 0 to 25 wt %, advantageously 1 to 20 wt %, preferably 2 to 15 wt %, in particular 5 to 10 wt %,
optionally, solvents (preferably alcohols), advantageously 0 to 25 wt %, preferably 1 to 20 wt %, in particular 2 to 15 wt %,
"wt %" being based in each case on the total agent.

A particularly preferred liquid washing or cleaning agent usable according to the present invention contains, besides the 1-aza-3,7-dioxabicyclo[3.3.0]octane compound of the general formula (I), at least anionic surfactants in quantities from 0.5 to 20 wt %, nonionic surfactants in quantities from 1 to 25 wt %, builders in quantities from 1 to 25 wt %, enzymes, and water.

A further preferred washing or cleaning agent usable according to the present invention is a liquid fabric softener that, besides the 1-aza-3,7-dioxabicyclo[3.3.0] octane compound of the general formula (I), can preferably contain components that are selected from the following:
cationic surfactants such as, in particular, esterquats, e.g. in quantities from 5 to 30 wt %,
co-surfactants such as, in particular, glycerol monostearate, stearic acid, fatty alcohols, and/or fatty alcohol ethoxylates, e.g. in quantities from 0 to 5 wt %, preferably 0.1 to 4 wt %,
emulsifier agents such as, for example, fatty amine ethoxylates, e.g. in quantities from 0 to 4 wt %, preferably 0.1 to 3 wt %,
optionally, further fragrances,
optionally, dyes, preferably in the ppm range,
solvents such as, in particular, water, e.g. in quantities from 60 to 90 wt %,
"wt %" being based in each case on the total agent.

A further subject of the invention is a method for degrading off-odors on textiles in the context of a textile treatment method, in which method the textile is exposed, in a manual or mechanical washing or soaking process employing a washing, cleaning, or care-providing agent containing a 1-aza-3,7-dioxabicyclo[3.3.0]octane compound of the general formula (I) usable according to the present invention, preferably in quantities from 0.0001 to 5 wt % based on the total agent, to a washing bath, the temperature of the washing bath being 5 to 95° C., preferably 10 to 60° C., and in particular 15 to 40° C.

EXAMPLES

Example 1

An experimental container having a capacity of 35 liters was equipped with a 1-cm opening for attachment of a hose with which an olfactory check of the atmosphere present therein could take place. Using a lateral hatch near the bottom, the container could be quickly opened and populated with investigative media. The experiment took place at room temperature under standard pressure. Two identically configured containers were used. A Petri dish having 5 mL of a 10-percent off-odor solution A (in polyethylene glycol 2000) was placed into the cleaned and odor-neutral containers. This off-odor solution A (see formula below) serves to reconstruct an off-odor that is usual for toilet areas. After one hour, the Petri dish having the standard was removed. After 30 minutes, an olfactory check of each the two containers yielded an intense odor of the toilet off-odor. A test solution [see below: methyl serinol solution plus aldehyde C10, as well as oxazolidine solution (bicyclic oxazolidine formed by reacting aldehyde C10 with methyl serinol)] was introduced in finely distributed form into one of the experimental containers by means of a spray bottle. One spray burst having a volume of 0.1 mL was generated in each case. The solvent used was ethanol. The solutions had a 10-percent active agent content. The test solutions therefore differed only in that for the oxazolidine solution, the reaction product of a reaction of aldehyde C10 with methyl serinol (i.e. the oxazolidine) was present, whereas for the methyl serinol solution plus aldehyde C10, the amino alcohol and the fragrance aldehyde were present separately. Immediately after the spray burst and at the time intervals indicated in the table, an assessment of the odor intensity of the toilet off-odor in the chamber was carried out. The scale of odor intensity extends from strong (score 10) to barely perceptible (score 1). The assessment was performed by people with olfactory training.

Results:

|  | Intensity after 0 hr | Intensity after 1 hr | Intensity after 2 hr | Intensity after 4 hr | Intensity after 8 hr |
| --- | --- | --- | --- | --- | --- |
| Chamber without further treatment | 10 | 6 | 6 | 5 | 4 |
| Chamber treated with methyl serinol solution plus aldehyde C10 | 10 | 4 | 2 | 1 | 0 |
| Chamber treated with oxazolidine solution | 10 | 3 | 1 | 0 | 0 |

As shown by the experimental results, after only 4 hours the oxazolidine resulted in complete extinction of the off-odor. In the case of the methyl serinol solution (methyl serinol solution plus aldehyde C10), odor extinction was achieved only after twice as long a period, i.e. after 8 hours.

The addition of oxazolidines to the system made possible, all in all, efficient extinction of off-odors.

| Off-odor solution A (toilet) | |
| --- | --- |
| 3-Methylbutanoic acid | 20 wt % |
| n-Butanoic acid | 20 wt % |
| n-Hexanoic acid | 20 wt % |
| 2,3-Benzopyrrole | 20 wt % |
| 4-Methyl-2,3-benzopyrrole | 10 wt % |
| Ammonia solution (25% in water) | 10 wt % |

Example 2

For evaluation, a variety of off-odor standards for bad odors were utilized. Standard perspiration (off-odor solution B (see formula below), serving to reconstruct a perspiration off-odor) represented a perspiration odor proceeding from humans; standard toilet (off-odor solution A, see above) represented the bad smell in toilet areas; and standard mildew (off-odor solution C (see formula below)) represented a mildew odor that is typical of poorly ventilated basement areas.

In a screw-top jar having a defined volume of 2 L, a respective textile 10×10 cm in size, provided with an off-odor (standard perspiration, toilet, or mildew) was secured on the screw top with adhesive hook-and-loop tape. Each textile was loaded for this purpose with 38 mg of the relevant off-odor standard. The loaded textile was then introduced into the screw-top jar and then ripened therein for 2 hours with the top closed. Then 35 g of each test solution was introduced [serinol solution or methyl serinol solution plus aldehyde C10, as well as oxazolidine solution (bicyclic oxazolidine formed by reacting aldehyde C10 with serinol or methyl serinol)]. The test solutions were prepared as molar solutions in ethanol. The test solutions once again differed only in that in the case of the oxazolidine solutions, the reaction product of fragrance aldehyde and amino alcohol, i.e. the oxazolidine, was present, whereas in the comparison cases the amino alcohol and the fragrance aldehyde were present separately. The odor was then assessed over a period of 24 hours by people with olfactory training. Polyester and cotton were used as textiles (see below).

Results:

Standard perspiration on polyester

| | Intensity after 0 hr | Intensity after 2 hr | Intensity after 4 hr | Intensity after 6 hr | Intensity after 24 hr |
|---|---|---|---|---|---|
| Standard perspiration | 10 | 9 | 7 | 6 | 3 |
| Oxazolidone made up of serinol and aldehyde C10 | 10 | 3 | 2 | 1 | 0 |
| Aldehyde C10 plus serinol | 10 | 3 | 3 | 2 | 1 |

Standard toilet on polyester

| | Intensity after 0 hr | Intensity after 2 hr | Intensity after 4 hr | Intensity after 6 hr | Intensity after 24 hr |
|---|---|---|---|---|---|
| Standard toilet | 10 | 9 | 8 | 8 | 7 |
| Oxazolidone made up of serinol and aldehyde C10 | 10 | 6 | 4 | 3 | 3 |
| Aldehyde C10 plus serinol | 10 | 7 | 6 | 4 | 4 |

Standard perspiration on cotton

| | Intensity after 0 hr | Intensity after 2 hr | Intensity after 4 hr | Intensity after 6 hr | Intensity after 24 hr |
|---|---|---|---|---|---|
| Standard perspiration | 10 | 9 | 5 | 4 | 2 |
| Oxazolidone made up of serinol and aldehyde C10 | 10 | 3 | 1 | 1 | 0 |
| Aldehyde C10 plus serinol | 10 | 3 | 3 | 2 | 1 |

Standard mildew on cotton

| | Intensity after 0 hr | Intensity after 2 hr | Intensity after 4 hr | Intensity after 6 hr | Intensity after 24 hr |
|---|---|---|---|---|---|
| Standard mildew | 10 | 9 | 8 | 8 | 3 |
| Oxazolidine made up of serinol and aldehyde C10 | 10 | 4 | 2 | 1 | 0 |
| Aldehyde C10 plus serinol | 10 | 5 | 4 | 3 | 2 |

Here as well, all the examples show the superior effect of the oxazolidines in counteracting off-odors, as compared with the combination of fragrance aldehyde and amino alcohol.

Off-odor solution B (perspiration)

| | |
|---|---|
| Octanoic acid | 20 wt % |
| Nonanoic acid | 20 wt % |
| 3-Methylbutanoic acid | 20 wt % |
| 2-Ethyl-2-hexenoic acid | 20 wt % |
| 3-Mercapto-1-hexanol | 20 wt % |

Off-odor solution C (mildew)

| | |
|---|---|
| Patchouli (essential oil) | 10 wt % |
| Geosmin (0.1% in DPG) | 10 wt % |
| Fixolide | 10 wt % |
| Terpineol-4 | 10 wt % |
| n-Hexanoic acid | 20 wt % |
| 3-Methylbutanoic acid | 20 wt % |
| 4-Ethyloctanoic acid | 20 wt % |

Fixolide: (+)-1-[(6S)-3,5,5,6,8,8-hexamethyl-5,6,7,8-tetrahydronaphthalen-2-yl]ethanone Geosmin: (4S,4aS,8aR)-4,8a-dimethyl-1,2,3,4,5,6,7,8-octahydronaphthalen-4a-ol While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for degrading off-odors from amine derivatives and sulfur derivatives by employing a 1-aza-3,7-dioxabicyclo[3.3.0]octane compound of the general formula (I)

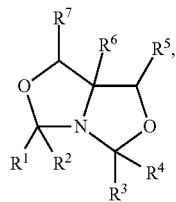

wherein
$R^1$, $R^2$, $R^3$, $R^4$ mutually independently denote residues that, in a compound of the general formula $R^1$—C(=O)—$R^2$ or $R^3$—C(=O)—$R^4$, yield a fragrance aldehyde having at least six carbon atoms or a fragrance ketone having at least six carbon atom,
$R^5$, $R^6$, $R^7$ mutually independently denote H or a hydrocarbon residue that can be acyclic or cyclic, substituted or unsubstituted, branched or unbranched as well as saturated or unsaturated
whereby the off-odor is deactivated.

2. The method according to claim 1, wherein the fragrance aldehyde is selected from the group consisting of adoxal (2,6,10-trimethyl-9-undecenal), anisaldehyde (4-methoxybenzaldehyde), cymal (3-(4-isopropylphenyl)-2-methylpropanal), ethyl vanillin, florhydral (3-(3-isopropylphenyl)butanal), helional (3-(3,4-methylenedioxyphenyl)-2-methylpropanal), heliotropin, hydroxycitronellal, lauraldehyde, lyral (3- and 4-(4-hydroxy-4-methyl pentyl)-3-cyclohexene-1-carboxaldehyde), methyl nonyl acetaldehyde, lilial (3-(4-tert-butylphenyl)-2-methylpropanal), phenyl acetaldehyde, undecylenealdehyde, vanillin, 2,6,10-trimethyl-9-undecenal, 3-dodecen-1-al, alpha-n-amylcinnamaldehyde, melonal (2,6-dimethyl-5-heptenal), 2,4-dimethyl-3-cyclohexene-1-carboxaldehyde (triplal), 4-methoxybenzaldehyde, benzaldehyde, 3-(4-tert-butylphenyl)propanal, 2-methyl-3-(para-methoxyphenyl)propanal, 2-methyl-4-(2,6,6-trimethyl-2(1)-cyclohexen-1-yl)butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzylaldehyde, 1,2,3,4,5,6,7,8-octahydro-8,8-dimethyl-2-naphthaldehyde, 2,4-dimethyl-3-cyclohexene-1-carboxaldehyde, 2-methyl-3-(isopropylphenyl)propanal, 1-decanal, 2,6-dimethyl-5-heptenal, 4-(tricyclo[5.2.1.0(2,6)]-decylidene-8)-butanal, octahydro-4,7-methane-1H-indenecarboxaldehyde, 3-ethoxy-4-hydroxybenzaldehyde, para-ethyl-alpha,alpha-dimethylhydrocinnamaldehyde, alpha-methyl-3,4-(methylenedioxy)hydrocinnamaldehyde, 3,4-methylenedioxybenzaldehyde, alpha-n-hexylcinnamaldehyde, m-cymene-7-carboxaldehyde, alpha-methyl phenyl acetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3-cyclohexenecarboxaldehyde, 1-dodecanal, 2,4-dimethylcyclohexene-3-carboxaldehyde, 4-(4-hydroxy-4-methyl pentyl)-3-cylohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tert-butyl)propanal, dihydrocinnamaldehyde, 1-methyl-4-(4-methyl-3-pentenyl)-3-cyclohexene-1-carboxaldehyde, 5- or 6-methoxyhexahydro-4,7-methane indane-1- or -2-carboxaldehyde, 3,7-dimethyloctan-1-al, 1-undecanal, 10-undecen-1-al, 4-hydroxy-3-methoxybenzaldehyde, 1-methyl-3-(4-methylpentyl)-3-cyclohexenecarboxaldehyde, 7-hydroxy-3,7-dimethyloctanal, trans-4-decenal, 2,6-nonadienal, para-tolylacetaldehyde, 4-methyl phenyl acetaldehyde, 2-methyl-4-(2,6,6-trimethyl-1-cyclohexen-1-yl)-2-butenal, ortho-methoxycinnamaldehyde, 3,5,6-trimethyl-3-cyclohexenecarboxaldehyde, 3,7-dimethyl-2-methylene-6-octenal, phenoxyacetaldehyde, 5, 9-dimethyl-4,8-decadienal, peony aldehyde (6,10-dimethyl-3-oxa-5,9-undecadien-1-al), hexahydro-4,7-methane indane-1-carboxaldehyde, 2-methyloctanal, alpha-methyl-4-(1-methyl ethyl)benzeneacetaldehyde, 6,6-dimethyl-2-norpinene-2-propionaldehyde, para-methyl phenoxy acetaldehyde, 2-methyl-3-phenyl-2-propen-1-al, 3,5,5-trimethylhexanal, hexahydro-8,8-dimethyl-2-naphthaldehyde, 3-propylbicyclo [2.2.1]-hept-5-ene-2-carbaldehyde, 9-decenal, 3-methyl-5-phenyl-1-pentanal, methyl nonyl acetaldehyde, hexanal, and trans-2-hexenal.

3. The method according to claim 1, wherein the fragrance ketone is selected from the group consisting of methyl beta-naphthyl ketone, musk indanone (1,2,3,5,6,7-hexahydro-1,1,2,3,3-pentamethyl-4H-inden-4-one), tonalide (6-acetyl-1,1,2,4,4,7-hexamethyltetraline), alpha-damascone, beta-damascone, delta-damascone, isodamascone, damascenone, methyl dihydrojasmonate, menthone, carvone, camphor, koavone (3,4,5,6,6-pentamethylhept-3-en-2-one), fenchone, alpha-ionone, beta-ionone, gamma-methyl ionone, fleuramone (2-heptylcyclopentanone), dihydrojasmone, cis-jasmon, iso-E-super (1-(1,2,3,4,5,6,7,8-octahydro-2,3,8,8-tetramethyl-2-naphthalenyl)-ethan-1-one
(and isomers)), methyl cedrenyl ketone, acetophenone, methyl acetophenone, para-methoxyacetophenone, methyl beta-naphthyl ketone, benzylacetone, benzophenone, para-hydroxyphenyl butanone, celery ketone (3-methyl-5-propyl-2-cyclohexenone), 6-isopropyldecahydro-2-naphthone, dimethyl octenone, Frescomenthe (2-butan-2-yl-cyclohexan-1-one), 4-(1-ethoxyvinyl)-3,3,5,5-tetramethylcyclohexanone, methyl heptenone, 2-(2-(4-methyl-3-cyclohexen-1-yl)propyl)cyclopentanone, 1-(p-menthen-6(2)yl)-1-propanone, 4-(4-hydroxy-3-methoxyphenyl)-2-butanone, 2-acetyl-3,3-dimethylnorbornane, 6,7-dihydro-1,1,2,3,3-pentamethyl-4(5H)-indanone, 4-damascol, dulcinyl (4-(1,3-benzodioxol-5-yl)butan-2-one), hexalone (1-(2,6,6-trimethyl-2-cyclohexen-1-yl)-1,6-heptadien-3-one),
isocyclemone E (2-acetonaphthone-1,2,3,4,5,6,7,8-octahydro-2,3,8,8-tetramethyl), methyl nonyl ketone, methyl cyclocitrone, methyl lavender ketone, orivone (4-tert-amyl cyclohexanone), 4-tert-butyl cyclohexanone, delphone (2-pentylcyclopentanone), muscone (CAS 541-91-3), neobutenone (1-(5,5-dimethyl-1-cyclohexenyl)pent-4-en-1-one), plicatone (CAS 41724-19-0), veloutone (2,2,5-trimethyl-5-pentylcyclopentan-1-one), 2,4,4,7-tetramethyloct-6-en-3-one, and tetrameran (6,10-dimethylundecen-2-one).

4. The method according to claim 1, wherein in the 1-aza-3,7-dioxabicyclo[3.3.0]octane compound of the general formula (I), the residues $R^5$ and IC mutually independently each denote hydrogen or a $C_{1-6}$ hydrocarbon residue that can optionally be substituted.

5. The method according to claim 1, wherein in the 1-aza-3,7-dioxabicyclo[3.3.0]octane compound of the general formula (I), the residue $R^6$ denotes a methyl, ethyl, or hydroxymethyl residue, or hydrogen.

6. The method according to claim 1, wherein in the 1-aza-3,7-dioxabicyclo[3.3.0]octane compound of the general formula (I), the residues $R^2$ and $R^4$ each denote hydrogen.

7. The method according to claim 1, wherein in the 1-aza-3,7-dioxabicyclo[3.3.0]octane compound of the general formula (I), the residues $R^2$, $R^4$, $R^5$, IC each denote hydrogen and the residue $R^6$ denotes a methyl, ethyl, or hydroxymethyl residue or hydrogen; and that the residues $R^1$ and $R^3$ mutually independently each denote a $C_{6-24}$ hydrocarbon residue.

8. The method according to claim 1, wherein the off-odors are present on hard and/or soft surfaces.

9. The method according to claim 1 for degrading off-odors on textiles, in the context of a textile treatment method in which the textile is exposed, in a manual or mechanical washing or soaking process, to a washing bath that contains a 1-aza-3,7-dioxabicyclo[3.3.0]octane compound of the general formula (I), where the temperature of the washing bath is 5 to 95° C.

10. The method according to claim 1 for degrading off-odors on textiles, in which method a liquid containing a 1-aza-3,7-dioxabicyclo[3.3.0]octane compound of the general formula (I) is sprayed onto the textile.

11. The method according to claim 1 for degrading off-odors on hard surfaces, in which method the hard surface is brought into contact with a liquid containing a 1-aza-3,7-dioxabicyclo[3.3.0]octane compound of the general formula (I), by rinsing and/or spraying.

12. The method according to claim 1 for degrading the effect of off-odors in room air, where the 1-aza-3,7-dioxabicyclo[3.3.0]octane compound of the general formula (I) is introduced into the room air via sticks, cards, blocks, or spray.

\* \* \* \* \*